(12) United States Patent
Buzek et al.

(10) Patent No.: US 11,035,773 B2
(45) Date of Patent: Jun. 15, 2021

(54) TORSIONAL RHEOMETER THAT MAINTAINS A MORE UNIFORM CAVITY PRESSURE

(71) Applicant: ALPHA TECHNOLOGIES SERVICES LLC, Akron, OH (US)

(72) Inventors: Keith Buzek, Akron, OH (US); Edward Norton, Munroe Falls, OH (US)

(73) Assignee: ALPHA TECHNOLOGIES SERVICES LLC, Akron, OH (US)

(*) Notice: Subject to any disclaimer, the term of this patent is extended or adjusted under 35 U.S.C. 154(b) by 0 days.

(21) Appl. No.: 16/909,217

(22) Filed: Jun. 23, 2020

(65) Prior Publication Data

US 2020/0319072 A1    Oct. 8, 2020

Related U.S. Application Data

(62) Division of application No. 15/764,450, filed as application No. PCT/US2016/054343 on Sep. 29, 2016, now abandoned.

(60) Provisional application No. 62/234,967, filed on Sep. 30, 2015.

(51) Int. Cl.
  *G01N 11/16* (2006.01)
  *G01N 33/44* (2006.01)

(52) U.S. Cl.
  CPC ......... *G01N 11/165* (2013.01); *G01N 33/442* (2013.01); *G01N 2203/0092* (2013.01)

(58) Field of Classification Search
  CPC ... G01N 11/162; G01N 11/165; G01N 33/442
  See application file for complete search history.

(56) References Cited

U.S. PATENT DOCUMENTS

| | | |
|---|---|---|
| 5,277,058 A | 1/1994 | Kalyon et al. |
| 6,523,397 B1 | 2/2003 | Tosaki |
| 10,241,019 B2 | 3/2019 | Jamison et al. |
| 2007/0220990 A1 | 9/2007 | Putman et al. |
| 2017/0241885 A1 | 8/2017 | Buzek et al. |
| 2018/0017476 A1 | 1/2018 | Gajji et al. |
| 2018/0245635 A1 | 8/2018 | Platzek et al. |

FOREIGN PATENT DOCUMENTS

| | | |
|---|---|---|
| CA | 833240 A | 2/1970 |
| CN | 102072848 A | 5/2011 |
| CN | 103154699 A | 6/2013 |
| CN | 104364632 A | 2/2015 |
| KR | 0159582 B1 * | 5/1999 |
| WO | WO 01/22053 A1 * | 3/2001 |
| WO | 02059572 A1 | 8/2002 |

\* cited by examiner

*Primary Examiner* — John Fitzgerald
(74) *Attorney, Agent, or Firm* — Shumaker, Loop & Kendrick, LLP; James D. Miller

(57) ABSTRACT

A method and apparatus is disclosed for compensating for a reduction of die cavity pressure in a torsional rheometer caused by shrinkage of the test sample. In one embodiment, a compliant member is placed in series with load-bearing components of the rheometer. This compliant member deflects when pressure in the die cavity is reduced resulting in the die cavity becoming smaller to increase the pressure within the die cavity.

15 Claims, 5 Drawing Sheets

TORSIONAL RHEOMETER THAT MAINTAINS A MORE UNIFORM CAVITY PRESSURE

CROSS REFERENCE TO RELATED PATENT APPLICATION

This patent application is a divisional patent application of U.S. patent application Ser. No. 15/764,450 filed Mar. 29, 2018, which in turns claims the benefit of PCT Patent Appl. Ser. No. PCT/US2016/054343 filed on Sep. 29, 2016, and U.S. Provisional Appl. Ser. No. 62/234,967 filed on Sep. 30, 2015. The entire contents of each of which are hereby incorporated herein by reference.

FIELD

Aspects herein generally relate to rheometer systems for testing polymers, and more particularly to a torsional rheometer system that compensates for shrinkage of a test sample to maintain a more uniform cavity pressure.

BACKGROUND

Polymers are often tested in accordance with one of several ASTM methods. Examples include ASTM D6048, D5289, D6204, D6601, D7050 and D7605. ASTM 6204 describes the use of a variable frequency test and also discloses the capability of performing a variable temperature test. ASTM D6601 describes the conditions for evaluating a specimen at more than one strain amplitude during a single test. Instruments operating in accordance with these ASTM tests are known.

Existing torsional rheometers include an upper die, an upper housing, and an upper seal plate (upper assembly), and a lower die, a lower housing and a lower seal plate (lower assembly). One example of an existing torsional rheometer is the RPA 2000 sold by Alpha Technologies, Inc. The RPA 2000 is a dynamic mechanical rheological tester (DMRT) designed to test raw elastomers or mixed rubber before, during and after cure in a single test. During a test, the upper assembly is lowered onto the lower assembly that contains an excess amount of a test specimen. A closing force, which may be in one example approximately 3500 pounds force, squeezes the polymer sample and forms a sealed die cavity with the sample under pressure between the upper and lower dies. The closing force is distributed between the polymer sample in the die cavity and the seal plate housing. The faces of the upper and lower seal plates come into direct contact with each other which then holds the faces of the upper and lower dies a fixed distance apart. This typically produces a die cavity pressure near 1000 psi. but the pressure can vary due to factors such as the test temperature and the viscosity of the material. The lower die is then oscillated by a drive system and the force from the lower die is transmitted through the sample to the upper die where the resulting reaction torque is measured by a transducer mounted to the back of the upper die.

There are some rheological tests where it is beneficial to first run a subtest on the sample at an elevated temperature and then run an additional subtest at a reduced temperature. As the dies cool, the sample also cools, causing it to shrink, reducing the pressure in the die cavity. If the first test is a cure test, the sample often shrinks even more during the transition and there is a further loss of cavity pressure. At some point the polymer shrinkage becomes so severe that the interface between the die surface and the polymer breaks down, allowing the sample to slip on the die face and reducing the strain imparted to the material. This produces a reduction in the signal and often a shift in the peak phase of the signal relative to the lower die movement. Once this slippage occurs, the test results become inaccurate and often not repeatable.

SUMMARY OF INVENTION

One aspect relates to a torsional rheometer comprising a first die assembly having a first bearing surface, and a second die assembly having a second bearing surface facing the first bearing surface on the first die assembly to form a die cavity therebetween for placement of a test sample. The rheometer also comprises a first seal plate associated with the first die assembly, and a second seal plate associated with the second die assembly. The first and second seal plates are configured to capture and hold the test sample therebetween. The rheometer further comprises a force applicator configured to apply a load to urge the first die assembly against the second die assembly and to urge the first seal plate against the second seal plate to capture and hold the test sample in the die cavity, and at least one compliant member coupled to the second seal plate. The at least one compliant member is placed in series with other load-bearing components associated with the second die assembly, and the at least one compliant member is configured to deflect in response to a load being applied by the force applicator to the second seal plate.

Another aspect relates to a torsional rheometer which includes a first die assembly and a second die assembly, the second die assembly having a bearing surface facing a bearing surface on the first die assembly to form a die cavity therebetween for placement of a test sample, the rheometer further comprising a first seal plate associated with the first die assembly and a second seal plate associated with the second die assembly. The first and second seal plates are configured to capture and hold the test sample therebetween. The torsional rheometer also includes a force applying apparatus for applying a load to urge the first die assembly and second die assembly against one another and the first seal plate against the second seal plate to capture and hold the test sample in the die cavity. Also included is a housing assembly which supports the second seal plate and which bears at least a part of the load applied by the force applying apparatus to the second seal plate through the first seal plate, the housing assembly comprising a compliant member that is placed in series with the other load-bearing components associated with the second die assembly and that deflects when a load is applied by the force applying apparatus.

Another aspect relates to a method for compensating for reduction of cavity pressure due to shrinkage of a test sample in a die cavity of a torsional rheometer, the rheometer including at least one compliant member in series with load-bearing components of the rheometer. The method comprises acts of: (a) sealing a test sample in the die cavity, the die cavity having a first size, and (b) decreasing the die cavity to a second size that is smaller than the first size by deflecting the at least one compliant member in response to a pressure drop and/or shrinkage of the test sample in the die cavity.

Another aspect relates to a method for compensating for reduction of cavity pressure due to shrinkage of a test sample in a die cavity of a torsional rheometer which comprises placing a compliant member in series with load-bearing components of a rheometer such that when pressure drops in the die cavity, the compliant member deflects causing a size of the die cavity to become smaller and a pressure in the die cavity to increase.

BRIEF DESCRIPTION OF THE DRAWINGS

The accompanying drawings are not intended to be drawn to scale. In the drawings, each identical and nearly-identical component that is illustrated in various figures is represented by a like numeral. For purposes of clarity, not every component may be labeled in every drawing. Various embodiments of the invention will now be described by way of example with reference to the accompanying drawings, in which.

DETAILED DESCRIPTION

This invention relates to an improved torsional rheometer system for testing polymers. One aspect of the invention relates to an apparatus that compensates for reduction in the pressure of the die cavity caused by shrinkage of the polymer sample in the die cavity during testing. This aspect includes a compliant member disposed in series with a load-bearing component in which the compliant member is configured to deflect as the pressure in the die cavity drops to cause the die cavity to close more tightly on the sample to maintain cavity pressure. This reduction in pressure may be caused by factors such as cooling of the test sample, curing of the test sample, or a lowering of the temperature used in a test. Another aspect relates to a method for compensating for reduction of cavity pressure in the die cavity of a torsional rheometer. This aspect includes placing a compliant member in series with the load-bearing components of the die cavity so that the compliant member deflects as cavity pressure drops to maintain cavity pressure during cooling.

Figure 1:
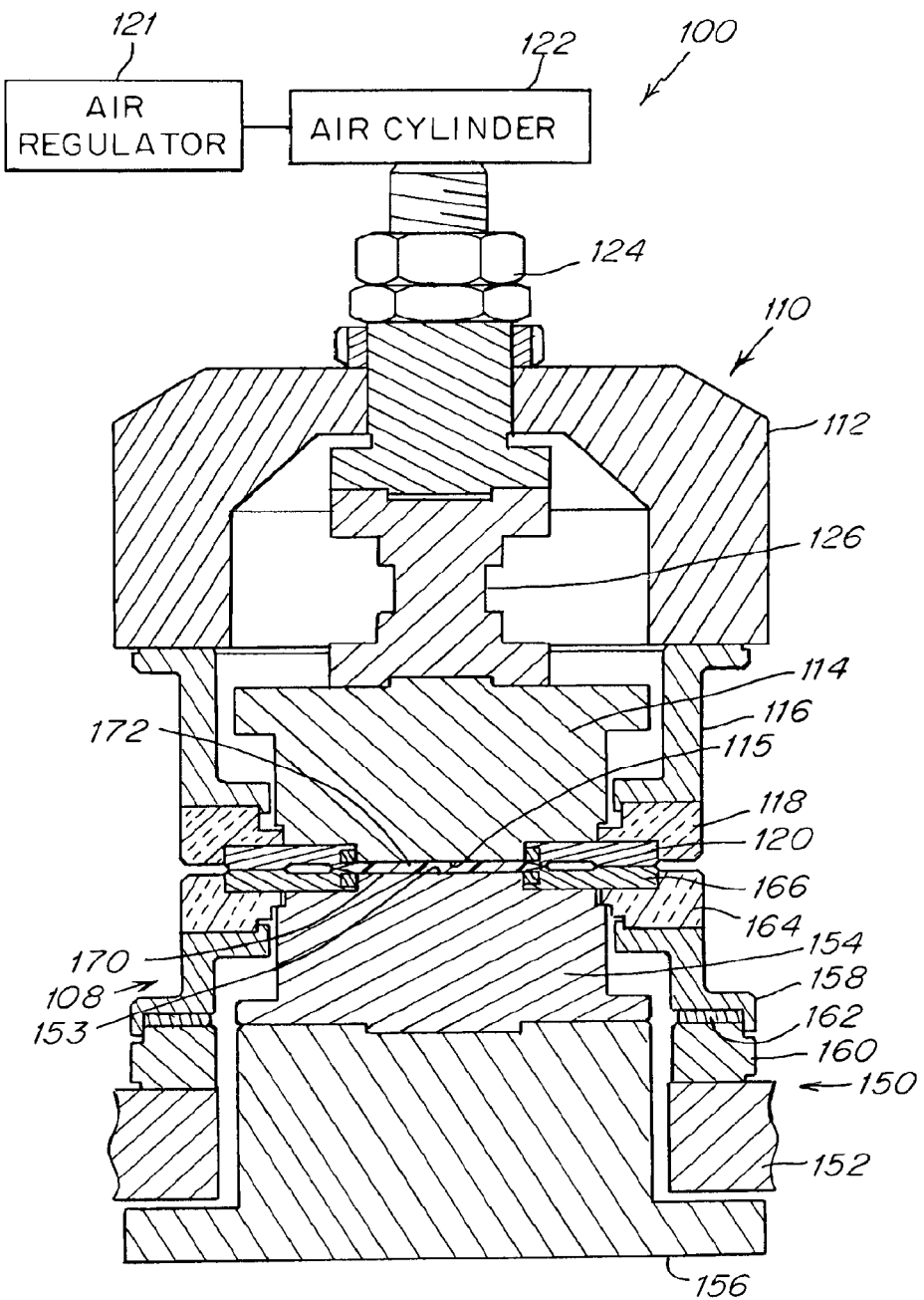
FIG. 1 is a partial, front, cross-sectional, schematic view of a prior art torsional rheometer.

With reference now to the drawings, and more particularly to FIG. 1 thereof, an example of a prior art torsional rheometer will now be described. FIG. 1 is a schematic representation of such a torsional rheometer, such as a RPA 2000 rheometer. FIG. 1 does not disclose all components thereof, but only the components necessary to gain an understanding of the invention. Furthermore, FIG. 1 is not drawn to scale or in a way that accurately represents the size and shape of each component.

Torsional rheometer 100 includes a first or upper assembly 110 and a second or lower assembly 150. Upper assembly 110 includes an upper cross-head 112, an upper die assembly 114, an upper seal plate housing 116, an upper insulator ring 118 and an upper seal plate 120. Upper cross-head 112 is driven upwardly and downwardly relative to lower assembly 150 by an air cylinder 122 which is shown schematically in FIG. 1. Air cylinder 122 is connected to upper cross-head 112 by a mount 124. Air cylinder 122 moves upper cross-head 112, and thus upper die assembly 114 toward and away from lower assembly 150 in a manner well-known to those of skill in the art. An air regulator 121 regulates the pressure applied by air cylinder 122. Torque and pressure transducers 126 are coupled to upper die assembly 114 to measure torque applied to upper die assembly 114 and pressure within the die cavity respectively.

Lower assembly 150 includes a fixed table plate 152 which supports and stabilizes rheometer 100. Lower assembly 150 also includes a lower die assembly 154. Lower die assembly 154 may be oscillated back and forth about its central axis by a drive motor 156. Surrounding lower die assembly 154 is a housing 108. Housing 108 includes an upper portion 158 and a lower portion 160. Disposed between upper portion 158 and lower portion 160 is a shim 162. Housing 108 rests on table plate 152. Sitting atop housing 108 is an insulator ring 164. Disposed on top of insulator ring 164 is a lower seal plate 166.

A die cavity 170 is disposed between lower surface 115 of upper die assembly 114, and upper surface 153 of lower die assembly 154. A test sample 172 may be placed in die cavity 170 and clamped between upper seal plate 120, and lower seal plate 166. Air cylinder 122 applies pressure to upper die assembly 114 to capture sample 172 between upper seal plate 120 and lower seal plate 166, and between surfaces 115 and 153. During a test, typically upper die assembly 114, and lower die assembly 154 are heated. To initiate a test, after insertion of test sample 172 into die cavity 170, the upper assembly 110 is lowered onto lower assembly 150. Initially, die cavity 172 contains an excess amount of a test sample. A closing force of approximately 3500 pounds force squeezes test sample 172 and forms a sealed die cavity 170 in which the sample is under pressure between both lower surface 115 of upper die assembly 114 and upper surface 153 of lower die assembly 154. Initially, this closing force is distributed between the force applied to sample 172 in die cavity 170 and the force applied by upper seal plate 120 to lower seal plate 166. This force typically produces a die cavity pressure near 1000 psi. However, this pressure can vary due to factors such as test temperature and the viscosity of the material. Lower die assembly 154 is then oscillated by drive motor 156, and the force from the lower die assembly 154 is transmitted through sample 172 to upper die assembly 114 where the resulting reaction torque is measured by transducer 126.

In some rheological tests, it is beneficial to first run a subtest on test sample 172 at an elevated temperature, and then run an additional subtest on sample 172 at a reduced temperature. As upper die assembly 114 and lower die assembly 154 are cooled, sample 172 also cools, causing it to shrink. If the first test is a cure test, sample 172 often shrinks even more during the transition. Both of these effects reduce the pressure in die cavity 170. At some point, the shrinkage of sample 172 may become so severe that the interfaces between sample 172 and surfaces 115 and 153 break down, allowing the sample to slip on surfaces 115 and 153, reducing the strain imparted to the material. This produces a reduction in the signal and often a shift in the peak phase of the signal relative to the movement of lower die assembly 154. Once the slippage occurs, the test results become inaccurate and often not repeatable.

Figure 2:
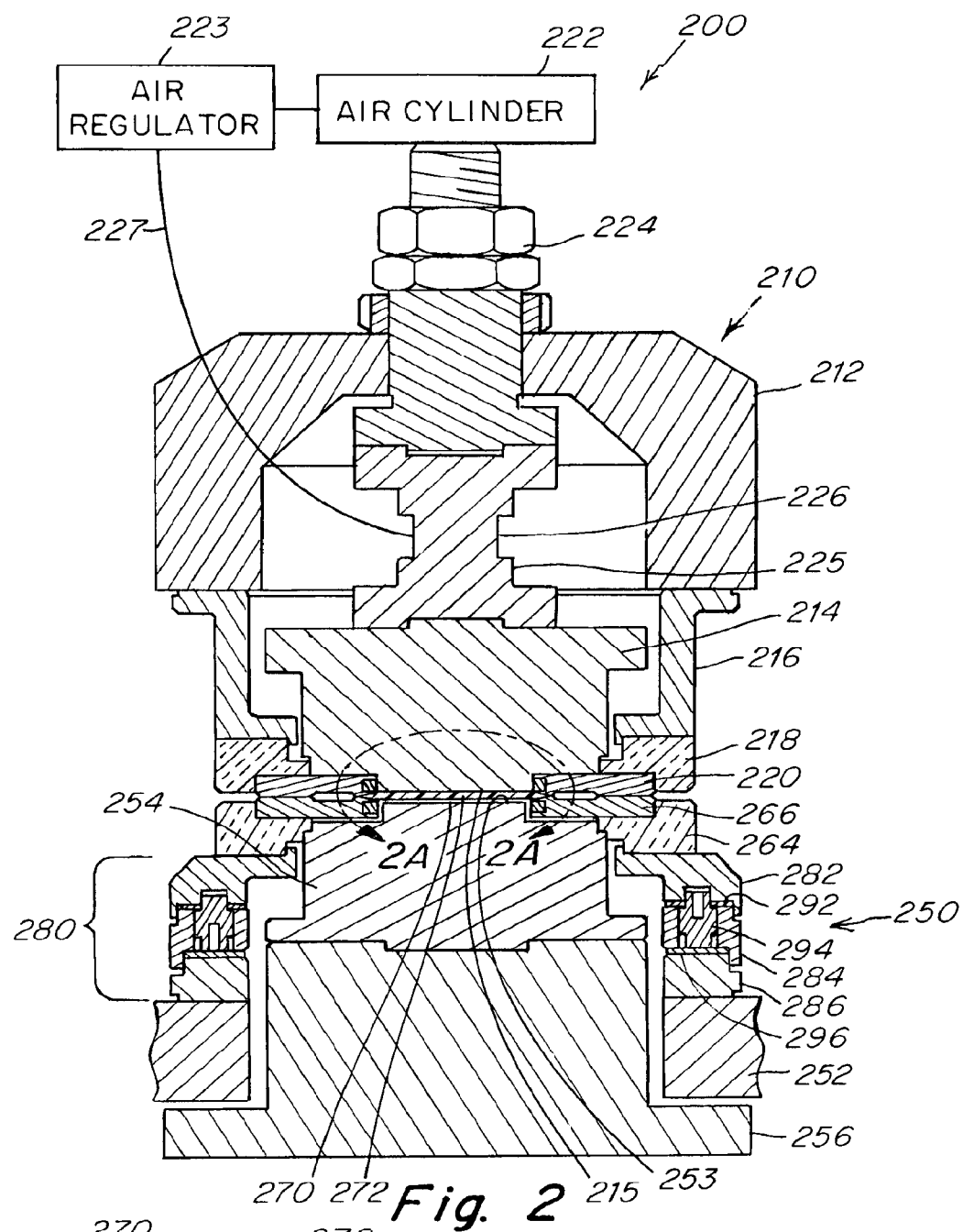
FIG. 2 is a partial, front, cross-sectional schematic view of a torsional rheometer in accordance with one aspect of the invention.
Figure 3:
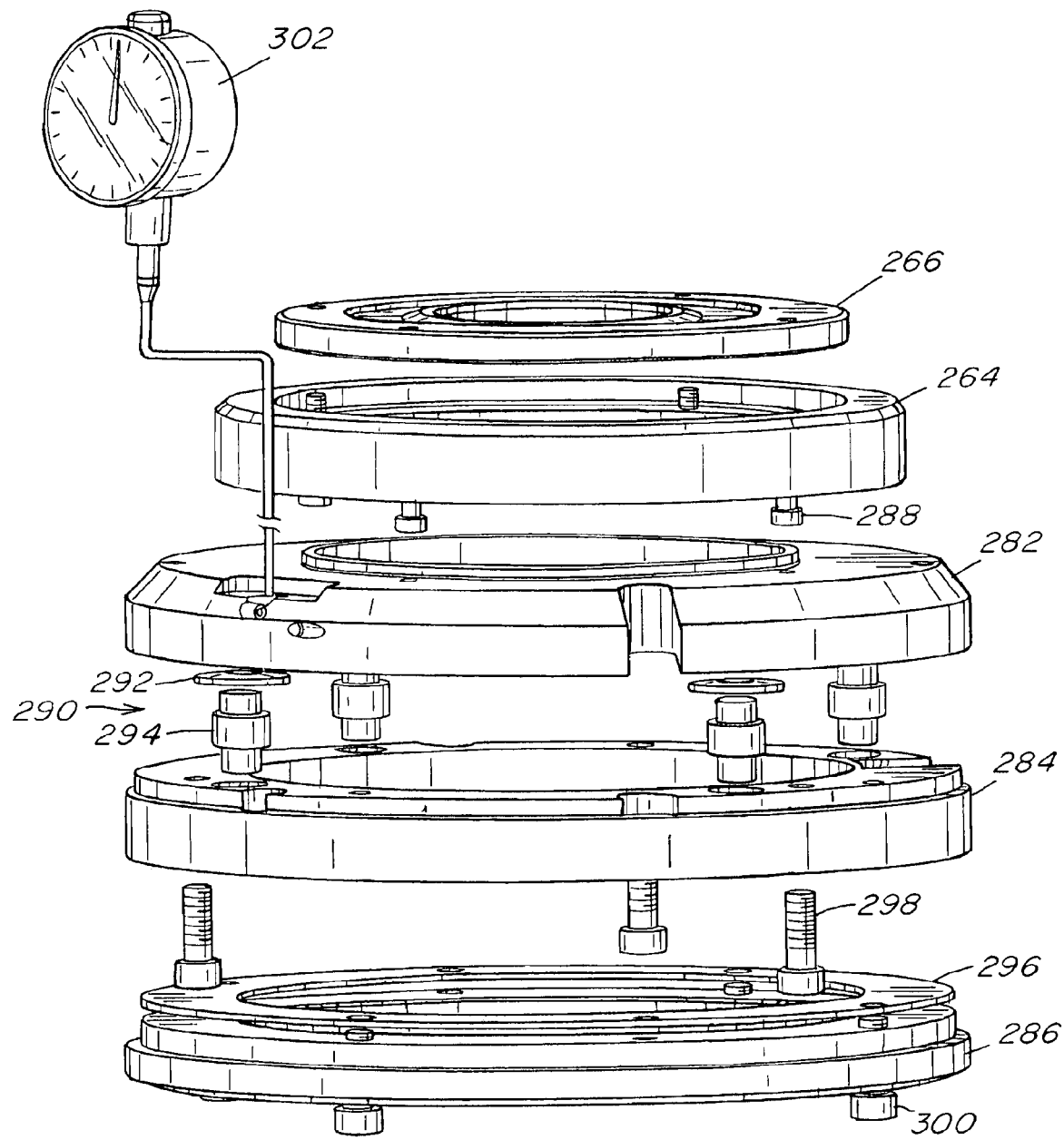
FIG. 3 is an exploded, perspective view of the lower housing assembly of the rheometer of FIG. 2.
Figure 4:
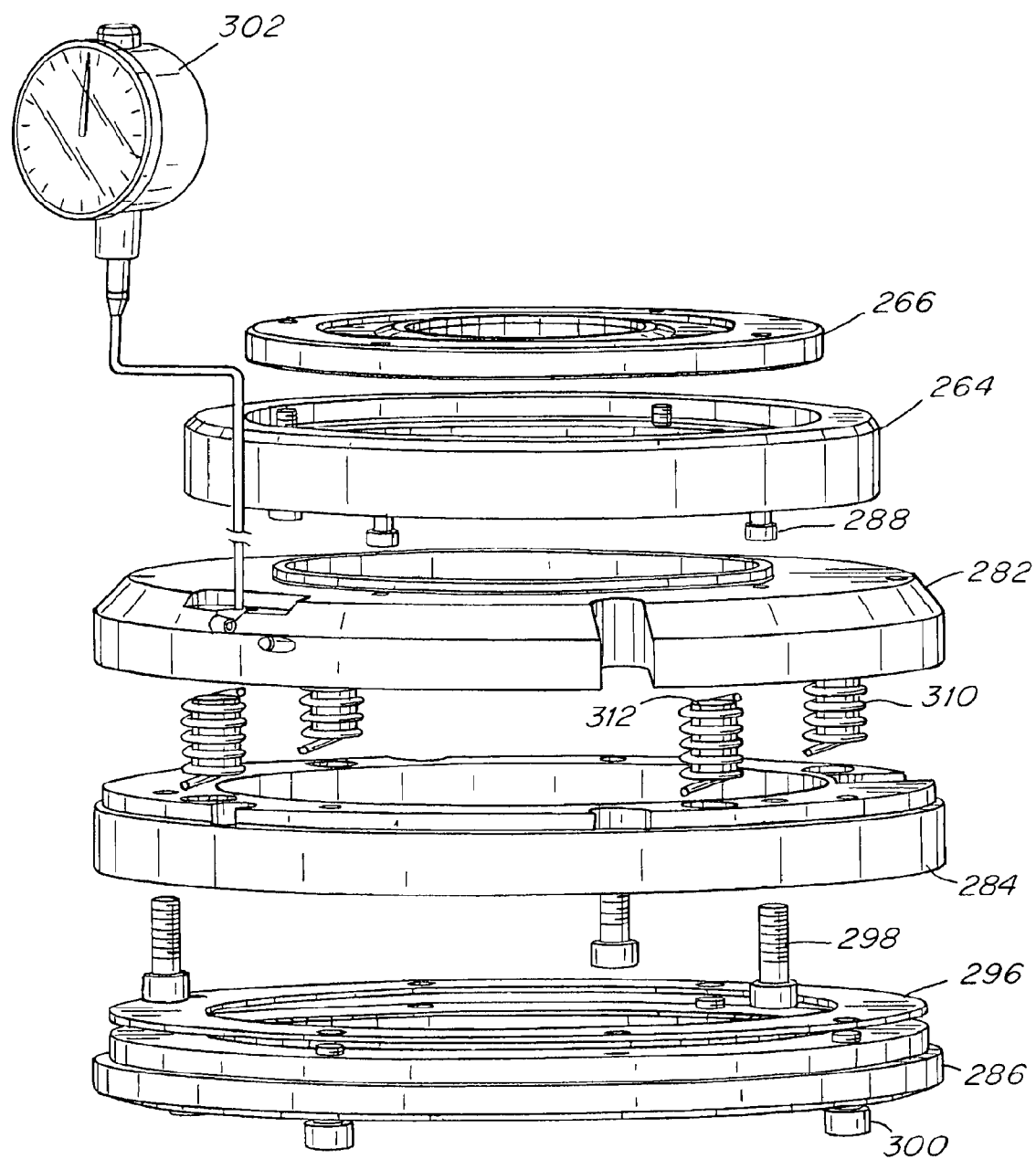
FIG. 4 is an exploded perspective view of another embodiment of the structure illustrated in FIG. 3.

These problems caused by reduction in die cavity pressure resulting from cooling and shrinkage of the sample in prior art torsional rheometers may be overcome by the improved torsional rheometer disclosed herein in FIGS. 2-4. FIG. 2 does not disclose all components of the torsional rheometer, but only the components material to an understanding of the invention. FIG. 2 also is not drawn to scale or in a way that accurately represents the size and shape of each component.

Torsional rheometer 200 of the present invention includes a first or upper assembly 210, and a second or lower assembly 250. Assembly 210 is substantially identical to assembly 110 of FIG. 1. Assembly 210 includes a cross-head 212, first die assembly 214, seal plate housing 216, insulator ring 218, and first seal plate 220. A force applying apparatus or force applicator, such as air cylinder 222, is coupled to cross-head 212 by mount 224, in a manner similar to that described with respect to FIG. 1, to move cross-head 212 and die assembly 214 toward and away from assembly 250. Torque transducer 225 and pressure transducer 226 are coupled to die assembly 214, and measure the reaction torque applied to die assembly 214 and pressure within die cavity 270, respectively.

In one embodiment, air cylinder 222 may be an 8-inch air cylinder, although other suitable air cylinders may be used. Air cylinder 222, in one embodiment, may apply 2500 pounds of force to the die assembly 214. In other embodiments, air cylinder 222 could be replaced with other drive apparatuses, such as an electric motor or a hydraulic drive system or the like. An air regulator 223 may control the pressure in air cylinder 222. In some embodiments, air regulator 223 may be programmed to maintain a desired pressure in cavity 270. In this embodiment, measurements of cavity pressure by transducers 226 may be provided to air regulator 223 in a feedback loop 225 to assist in maintaining the cavity pressure without human interaction.

The second or lower assembly 250 will now be described with respect to FIG. 2. As in FIG. 1, assembly 250 includes a fixed table plate 252 upon which rheometer 200 rests and which supports and stabilizes rheometer 200. Assembly 250 also includes a second die assembly 254, insulator ring 264 and a housing assembly 280. A drive motor 256 may be provided to produce oscillatory motion of die assembly 254 in the same manner as described with respect to FIG. 1. A second seal plate 266 rests on insulator ring 264. Die cavity 270 is disposed between a first bearing surface 215 of die assembly 214 and a second bearing surface 253 of die assembly 254. Test sample 272 may be placed in die cavity 270 and clamped between seal plate 220 and seal plate 266.

Figure 5:
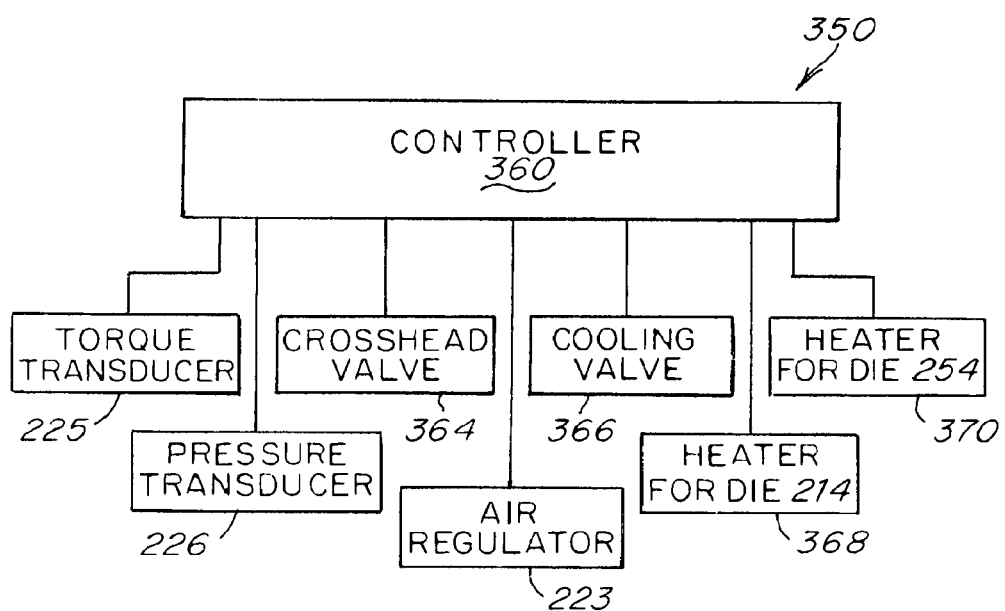
FIG. 5 is a schematic view of the control system of the torsional rheometer of FIG. 2.

The control system 350 for torsional rheometer 200 will now be described with respect to FIG. 5. Control system 350 includes controller 360, which may be any suitable controller. In one embodiment, the control functions are implemented in firmware executing on a circuit or processor. Controller 360 is connected to torque transducer 225 to receive and process measurements of the reaction torque applied to die assembly 214. Controller 360 is also coupled to pressure transducer 226 to receive and process measurements of the pressure within die cavity 270. Controller 360 is also coupled to air regulator 223 to control operation thereof. Cross-head 212 includes a valve 364 to which controller 360 is coupled. Valve 364, which in one embodiment, is a solenoid valve, is turned on and off by controller 360 to control the air supply to air cylinder 222. Both die assembly 214 and die assembly 254 are heated by an associated heater 368 and 370, respectively. Accordingly, controller 360 is coupled to heater 368 and to heater 370 to operate and control the heaters. Finally, a cooling system is provided for both die assembly 214 and die assembly 254 to allow performing tests at lower temperatures. This cooling system typically is forced air cooling, although other cooling systems may be used. Valve 366 turns the cooling system on and off, and is controlled by controller 360. Valve 366 may be a solenoid valve.

Figure 2A:
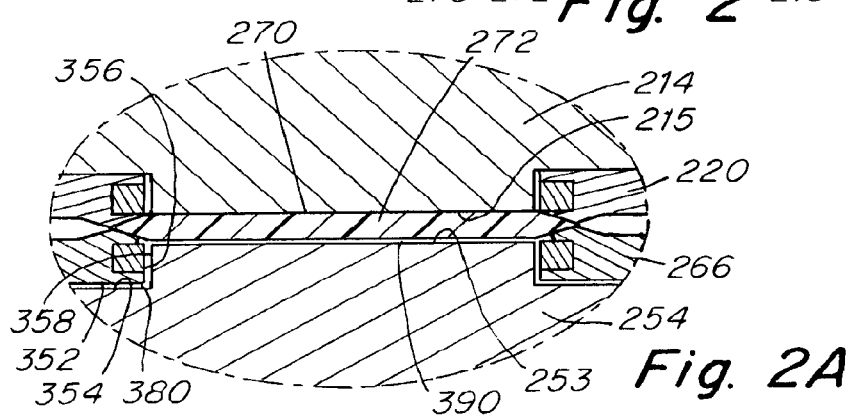
FIG. 2A is an enlarged, cross-sectional, schematic view of the cut out portion of FIG. 2.

As shown in FIGS. 2 and 2A, there may be a small gap 350 between a lower surface 352 of seal plate 266 and an upper, facing surface 354 of die assembly 254. Gap 350 permits movement of die assembly 254 toward and away from die assembly 214, as will be described. For this same reason, end faces 356 of seal plate 266 may be spaced from opposed faces 358 of die assembly 254. FIGS. 2 and 2A also illustrate a small space 360 that may appear in die cavity 270 as a result of shrinkage of sample 272.

Housing assembly 280 will now be described with respect to FIGS. 2 and 3. Housing assembly 280 may be disposed just below insulator ring 264, and may include upper plate 282, lower plate 286, and middle plate 284 disposed between upper plate 282 and lower plate 286. Disposed in housing assembly 280 are compliant members 290. Members 290 are placed in series with other load-bearing components of assembly 250, such as insulator ring 264, and/or the components of housing assembly 280. In the example shown in FIGS. 2 and 3, members 290 are disposed between upper plate 282 and middle plate 284, although members 290 could also be positioned between middle plate 284 and lower plate 286 or between upper plate 282 and insulator ring 264 or between lower plate 286 and table 252. Members 290 are configured to deflect with increased load, as will be described more fully hereinafter.

Members 290 may be any suitable and known devices which will deflect a small amount when a large load is applied. In the example of FIG. 3, members 290 are shown to be spring washers 292, which are mounted on alignment pins 294. Spring washers 292 may be Belleville washers. In one embodiment, the Belleville washers may have a nominal spring rate of 44,679 pounds per inch, a working load of about 620 pounds, and a flat load of about 884 pounds. Deflection of these Belleville washers at a working load may be about 0.014 inches, in one example. Typically, in one embodiment, four spring washers 292 are used, however, in alternative embodiments, more or fewer washers 292 may be used. In an alternative embodiment, as shown in FIG. 4, coiled compression springs 310 mounted on pins 312 could be used. In other embodiments, members 290 may be machine springs, leaf springs, a polymer material, or a composite material. Members 290 may be comprised of any material that can be compressed as long as the material would support a working load of approximately 2500 pounds force. In other embodiments (not shown), a hydraulic system may be provided to raise housing assembly 280, to provide the function of members 290.

Positioned between middle plate 284 and lower plate 286, in some embodiments, may be a shim 296. Seal plate 266 may be attached to insulator ring 264 and to upper plate 282 by any known, suitable affixation devices. In one example, seal plate 266, insulator ring 264 and upper plate 282 are bonded together using screws 288 although it is to be understood that other affixation devices may be used. Typically, although not necessarily, screws 298 are used to attach middle plate 284 to upper plate 282. Finally, in one embodiment, screws 300 may attach lower plate 286 to middle plate 284. It should be understood, however, that other known means may be used to affix the plates together, such as glue, bolts, clips, or rivets.

In one embodiment, an indicator, such as dial indicator 302, may be provided to measure the deflection between plates 282 and 284.

In operation, initially die assembly 214 is separated from die assembly 254 by air cylinder 222. A test sample 272 may be placed in the cavity 270 so that it is substantially centered on die assembly 254. A closing force is applied to die assembly 214 by air cylinder 222. This closing force, in one embodiment, may be about 2500 pounds to 3000 pounds, and may cause test sample 272 to flow to fill die cavity 270 and then extend outwardly from die cavity 270 to lie between seal plate 220 and seal plate 266. A first test may be performed at a first temperature by actuating drive motor 256 and heating die assemblies 214 and 254 to a desired temperature. Thereafter, drive motor 256 oscillates die assembly 254 back and forth about a zero position along a central, vertical axis.

If there were no sample in die cavity 270, the load applied by air cylinder 222 would be transferred directly only to seal plate 266. As a result of this applied load, members 290 would be compressed, or deflected. In one embodiment where the closing force is 3000 pounds, this compression results in a gap of approximately 0.040 millimeters in die cavity 270. If a sample 272 is placed in die cavity 270, the same 3000 pound closing force is now divided between the force applied to sample 272 in die cavity 270, and seal plate 266 and ultimately members 290. In this example, 2000 pounds force may be applied to sample 272, which is then transferred to die assembly 254, and approximately 1000 pounds is applied to housing assembly 280. For this example, the force applied to housing assembly 280 is transferred to members 290 which causes a compression or deflection of members 290. If spring washers 292 are utilized, the resulting die gap is about 0.500 millimeters, in this example.

As sample 272 cools and shrinks, or if the sample 272 is cured and shrinks, the pressure in die cavity 270 drops. As a result, a greater portion of the closing force, applied by air cylinder 222, is transferred to housing assembly 280, and a lesser force is applied to sample 272. Thus, an additional force is applied to members 290 via seal plate 266 through housing assembly 280. Further deflection of members 290 occurs, causing die assembly 214 and thus lower surface 215 and seal plates 220 and 266 to move downwardly with respect to upper surface 253 of die assembly 254, which is stationary. This relative movement effectively reduces the size of die cavity 270, thus increasing the pressure in die cavity 270. This relative movement is permitted because of gaps 350 described above. In the example described above, in which 3000 pounds of force is applied by air cylinder 222, and in which spring washers 292 were used, the gap in die cavity becomes about 0.480 millimeters. Thus, members 290 may allow self-correction of the drop in die cavity pressure caused by shrinkage of sample 272.

In another embodiment, as illustrated in FIG. 2, the pressure within die cavity 270 may be measured by pressure transducer 226, and this information may be provided to air regulator 223 and controller 360 in a feedback loop 225. Air regulator 223 may be programmed to maintain the pressure within die cavity 270 at a desired value. Thus, as sample 272 shrinks due to changes in temperature or otherwise, and as the resulting pressure within die cavity 270 drops, a signal may be sent to air regulator 223 to increase the air pressure to air cylinder 222 which increases the pressure within die cavity 270. In one example, in which the initial applied force by air cylinder 222 is 3000 pounds, for a particular polymer, and for a significant temperature drop, the force applied by air cylinder 222 may be increased to about 4500 pounds. This sort of controlled feedback loop may assure that the optimum pressure is maintained at all times. This embodiment may be employed instead of or in addition to the self-correction embodiment described above. This embodiment may be required for higher torques and/or lower testing temperatures.

Yet another embodiment will now be described with respect to FIG. 2. Where significant cooling is expected or occurs during subsequent testing, or significant shrinkage of the sample 272 occurs, as noted above, the self-correcting technique may not be sufficient to maintain the pressure of die cavity 270 at the desired level. Moreover, for various reasons, it may not be desirable to include a feedback loop in the device to control a pre-programmed air regulator 223. In this embodiment, the amount of shrinkage to be expected in a particular polymer sample for a particular change in temperature may be empirically determined. In this way, air regulator 223 may be pre-programmed to apply greater or lesser pressure via air cylinder 222 on die assembly 214 at specified times in a testing cycle based upon the testing to be done and the sample being tested to maintain the cavity pressure.

It should be appreciated that while compliant member 290 has been shown as being provided on a portion of rheometer 200 which is on a side of die cavity 270 opposite from the side on which the force is applied by air cylinder 222, in other embodiments, compliant member 290 could be provided on the housing on the same side of die cavity 270 as the force is being applied by a cylinder 222. In other words, housing 216 could be provided with a structure similar to that of housing assembly 280, so that deflection of compliant members 290 would permit die assembly 214 and surface 215 thereof to move downwardly toward die assembly 254 to close the gap in die cavity 270. In this embodiment, a gap would need to be provided between an upper surface of seal plate 220, and a lower surface directly above seal plate 220 on die assembly 214 to accommodate movement of die assembly 214 with respect to seal plate 220. In most other respects, this embodiment would operate in substantially the same way as the embodiments described herein.

Use of ordinal terms such as "first," "second," "third," etc. in the claims to modify a claim element does not by itself connote any priority, precedence or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional terms.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example, unless otherwise indicated.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. It is not intended that the present teachings be limited to such embodiments or examples. Accordingly, the foregoing description and drawings are by way of example only.

What is claimed is:

1. A torsional rheometer comprising:
   a first die assembly having a first bearing surface;

a second die assembly having a second bearing surface facing the first bearing surface on the first die assembly to form a die cavity therebetween for placement of a test sample;

a first seal plate associated with the first die assembly;

a second seal plate associated with the second die assembly, the first and second seal plates being configured to capture and hold the test sample therebetween;

a force applicator configured to apply a load to urge the first die assembly against the second die assembly and to urge the first seal plate against the second seal plate to capture and hold the test sample in the die cavity; and at least one compliant member coupled to the second seal plate, the at least one compliant member placed in series with other load-bearing components associated with the second die assembly, the at least one compliant member configured to deflect in response to a load being applied by the force applicator to the second seal plate.

2. The torsional rheometer of claim 1, wherein a gap is located between the second seal plate and the second die assembly to permit movement of the second die assembly toward and away from the first die assembly when the test sample is captured and held in the die cavity.

3. The torsional rheometer of claim 1, wherein the at least one compliant member includes a plurality of compliant members.

4. The torsional rheometer of claim 3, wherein the plurality of compliant members are arranged in parallel with each other.

5. The torsional rheometer of claim 1, further comprising a housing assembly supporting the second seal plate, the housing assembly configured to bear at least part of the load applied by the force applicator to the second seal plate through the first seal plate, the housing assembly including the at least one compliant member.

6. The torsional rheometer of claim 5, wherein the housing assembly includes an upper plate, a lower plate and a middle plate located between the upper and lower plates.

7. The torsional rheometer of claim 6, wherein the at least one compliant member is located between the upper plate and the middle plate.

8. The torsional rheometer of claim 7, further comprising an indicator configured to measure deflection between the upper and middle plates.

9. The torsional rheometer of claim 1, wherein the at least one compliant member includes a spring.

10. The torsional rheometer of claim 9, wherein the spring includes a spring washer.

11. The torsional rheometer of claim 10, wherein the spring washer includes a Belleville washer.

12. The torsional rheometer of claim 10, wherein the spring includes a compression spring.

13. The torsional rheometer of claim 12, wherein the compression spring includes a coil spring.

14. A torsional rheometer comprising:
a first die assembly;
a second die assembly, the second die assembly having a bearing surface facing a bearing surface on the first die assembly to form a die cavity therebetween for placement of a test sample;
a first seal plate associated with the first die assembly;
a second seal plate associated with the second die assembly, the first and second seal plates being configured to capture and hold the test sample therebetween;
a force applying apparatus for applying a load to urge the first die assembly and second die assembly against one another and the first seal plate against the second seal plate to capture and hold the test sample in the die cavity; and
a housing assembly supporting the second seal plate, and bearing at least part of the load applied by the force applying apparatus to the second seal plate through the first seal plate, the housing assembly comprising a compliant member that is placed in series with the other load-bearing components associated with the second die assembly and that deflects when a load is applied by the force applying apparatus.

15. A method for compensating for reduction of cavity pressure due to shrinkage of a test sample in a die cavity of a torsional rheometer, the method comprising the steps of:
placing a compliant member in series with load-bearing components of the rheometer such that when pressure drops in the die cavity, the compliant member deflects causing a size of the die cavity to become smaller and a pressure in the die cavity to increase, wherein the compliant member is disposed between one of an upper plate and a middle plate, the middle plate and a lower plate, the upper plate and an insulator ring, or the lower plate and a table.

* * * * *